United States Patent [19]
Gourvest et al.

[11] Patent Number: 5,525,594
[45] Date of Patent: Jun. 11, 1996

[54] TREATMENT OF HYPERANDROGENIC DISORDERS

[75] Inventors: Jean-François Gourvest, Claye-Souilly, France; Alexander Kasal, Prague, Czech Rep.; Dominique Lesuisse, Paris; Jean-Georges Teutsch, Pantin, both of France

[73] Assignee: Roussel Uclaf, France

[21] Appl. No.: 340,025

[22] Filed: Nov. 14, 1994

[30] Foreign Application Priority Data

Nov. 16, 1993 [FR] France ................................. 93 13623

[51] Int. Cl.⁶ .......................... A61K 31/70; A61K 31/045
[52] U.S. Cl. ................... 514/25; 514/738; 536/4.1
[58] Field of Search ................. 424/195.1; 514/25, 514/738; 536/4.1

[56] References Cited

FOREIGN PATENT DOCUMENTS 0297547 1/1989 European Pat. Off. ......... A61K 3/70

OTHER PUBLICATIONS

Chem. Absts. 108:68525d, 1988.
Chem. Absts. 109:187326v, 1988.
Hatano, et al., J Chem Soc. Perkins Trans. 1, (1990), p. 2735.
Sendai, et al., Chem Phar Bull. (1989), 37(8): 2269–2271.
Copy of Journal of Liquid Chromatography, vol. 13(18), 1990, pp. 3637–3650.

*Primary Examiner*—John W. Rollins
*Attorney, Agent, or Firm*—Bierman & Muserlian

[57] ABSTRACT

A method of treating hyperandrogenism in warm-blooded animals comprising administering to warm-blooded animals an antiandrogenically effective amount of oenotheine B and a process for the preparation of oenotheine B.

3 Claims, No Drawings

TREATMENT OF HYPERANDROGENIC DISORDERS

STATE OF THE ART

Approximately 200 different species of Epilobium (Onagreaceae family) exist. *Epilobium parviflorum* as well as other species of Epilobium are described in traditional medicine as beneficial to all sorts of disorders such as those of the bladder, the kidney and more particularly the prostate [Hiermann, et al, J. Ethno-pharmacol., Vol. 17 (1986), pp. 161–167; TYLER, Pharm. Int. (1986) 205]. There are many constituents of Epilobium and they have complex structures. Several analyses have been attempted to date and show the existence of various types of compounds. However, the composition is still not well-known.

The presence of sterols [Hiermann, Sci. Pharm., Vol. 51 (1985), p. 39], triterpenes and flavonoids (aglycone and glycoside flavonols) (Hiermann, et al, Sci. Pharm., Vol. 51 (1983), p. 158) have thus been found. Recently, the separation of glycoside flavonols from *Epilobium parviflorum* has allowed the presence of quercitrin, myricitrin, isomyricitrin, gallic acid and chlorogenic acid to be revealed, (Slacanin, et al, J. Chrom., Vol. 557 (1991), p. 391–398).

OBJECTS OF THE INVENTION

It is an object of the invention to provide purified oenotheine B and a process for its preparation.

It is another object of the invention to provide novel antiandrogenic compositions and a method of treating hyperandrogenic activity in warm-blooded animals.

These and other objects and advantages of the invention will become obvious from the following detailed description.

THE INVENTION

Oenotheine B has been isolated from *Epilobium parviflorum* and is a hydrolyzable oligomeric tannin. It was isolated for the first time from *Oenothera erythrosepala* Borbas leaves (Hatano et al, J. Chem. Soc., Perkin Trans. 1, (1990), pp. 2735; 104th Annual Meeting of the Pharmaceutical Society of Japan, March 1984, Sendai et al Chem. Pharm. Bull. (1989), Vol. 37(8), pp. 2269–2271).

Oenotheine B was then found in various Onagreaceae plants and in *Woodfordia fruticosa* [Yoshida et al., Chem. Pharm. Bull., Vol. 38, pp. 1211 (1990)] which is part of the Lythraceae family. Finally, recently, oenotheine B was isolated from the dried fruit of the *Eucalyptus alba* REINW which is part of the Myrtaceae family (Yoshida et al., Chem. Pharm. Bull. (1992), Vol. 40(7), pp. 1750–1754).

Although discovered recently, oenotheine B has been the subject of many studies which have demonstrated its use as a medicament. Oenotheine B thus possesses a certain number of biological and pharmacological properties the antiviral and antitumour domain.

Antitumour activity:

Lead Chemical Co J62129220 (Nov. 6, 1987) Pr: 85JP-270494 (Nov. 30, 1985)

Nippon Kayaku Co J03123793 (May 5, 1991) Pr: 89JP-258708 (Oct. 5, 1989)

Ken-ichi Miyamoto et al., Biol. Pharm. Bull., Vol. 16(4), pp. 379–387 (1993)

A. Kuramochi-Motegi et al., Biochem. Pharm., Vol. 44(10), pp. 1961–1965 (1992)

Yan-Jyu Tsai et al., The Journal of Biological Chemistry, Vol. 267 (20), pp. 14436–14442

Ken-ichi Miyamoto et al., Jpn. J. Cancer Res., Vol. 84, pp. 99–103 (1993).

Antiviral activity (Herpes):

Fukuchi et al., Antiviral Research 11 (1989), pp. 285–298

Antiviral activity (HIV):

Lead Chemical Co EP-297547 (Jan. 4, 1989) Pr 87JP-161572 (Jun. 29, 1987).

It was during the study of a particular extract (aqueous fraction) from an *Epilobium parviflorum* decoction, that it was observed that the said extract responded significantly as an inhibitor of the testosterone enzyme 5-α-reductase, a key enzyme in the biosynthesis of certain androgens, particularly 4,5α-dihydro-testosterone (DHT). This observation led to an attempt to identify the molecule responsible for this inhibition which was shown to be oenotheine B.

In short, it is therefore the first time that oenotheine B has been isolated and identified as one of the active ingredients of *Epilobium parviflorum* and it is the first time that it has been determined that oenotheine B acts as an inhibitor of the testosterone enzyme, 5α-reductase, which was in no way foreseen from the prior art.

Oenotheine B has a specific activity as an inhibitor of 5α-reductase which is an enzyme responsible for the conversion of testosterone into dihydrotestosterone (DHT), which has a greater affinity than testosterone for the androgen receptor (AR). This hormone is essential in males, to the in utero development of the external sexual organs and then from puberty, to the appearance of certain secondary sexual characteristics (hair system of the face and body).

5α-reductase is found mainly in the prostate and in the skin, where it seems that testosterone must be converted into DHT to be active. An excess of DHT can be responsible for acne or androgenic alopecia, hirsutism in women, and its accumulation at the level of the prostate, for benign hyperplasia (BHP) or cancer of the prostate. It is estimated that 80% of men of more than 80 years old have a BHP and 70% have cancerous foci.

The inhibition of this enzymatic stage in steroid metabolism involves a fall in the level of DHT in vivo. This reduction of the level of DHT has the effect of reducing the size of the prostate in men and therefore has a beneficial effect in the treatment benign hyperplasia of the prostate, cancer of the prostate, and certain androgen-dependent illnesses.

A treatment inhibiting 5α-reductase is therefore very useful and does not present the disadvantages of an antiandrogen which blocks the receptor. This inhibiting property of 5α-reductase makes oenotheine B suitable to be used in the treatment of disorders linked to hyperandrogenism, particularly that of benign hyperplasia of the prostate (BHP), cancer of the prostate, acne, androgenic alopecia, seborrhea, or also female hirsutism.

Therefore, an object of the present invention is the use of oenotheine B to obtain a medicament intended for the treatment of disorders linked to hyperandrogenism. The dose varies as a function of the illness to be treated and the method of administration. It can vary from 5 to 100 mg/kg and, preferably, from 10 to 20 mg/kg per day in an adult orally.

The antiandrogenic compositions may be in the form of tablets, dragees, capsules, granules, suppositories, pessaries, ointments, creams, gels, patches and injectable solutions or suspensions.

Examples of suitable inert pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The novel method of the invention for treating hyperandrogenic activity in warm-blooded animals, including humans, comprises administering to warm-blooded animals an antiandrogenically effective amount of oenothoine B. The product may be administered orally, rectally or parentally.

The novel process of the invention for the preparation of oenotheine B comprises extracting dried samples of *Epilobium parviflorum* with water or a mixture of water and water-miscible solvents, filtering the extracts, optionally concentrating the extracts by evaporation of the water-miscible solvents under reduced pressure, subjecting the aqueous phase to a lyophilization or extracting the aqueous phase with a polar solvent and evaporating the extract to dryness to obtain a dry residue and purifying the lyophilizate or dry residue by reversed-phase HPLC or a polymer gel column to obtain oenothoine B.

Among preferred steps of the process are the following:

Extraction

Water or a mixture of water and solvents miscible with water such as alcohols chosen from methanol, ethanol, isopropanol, butanol, or acetone are added to dried samples of *Epilobium parviflorum*. They are preferably *Epilobium parviflorum* leaves. The preferred solvent miscible with water is acetone.

After stirring and filtration, the filtrate is optionally concentrated under reduced pressure until evaporation of the solvent miscible with water is obtained. The remaining aqueous phase is either lyophilized, or extracted with various polar organic solvents known to one skilled in the art such as diethyl ether, ethyl acetate or butanol. Butanol is preferably used. These fractions are then evaporated under reduced pressure at a temperature not exceeding 50° C., until a dry extract is obtained.

Purification

Purification of the active ingredient is carried out either by passage through a polymer gel column or by reversed-phase HPLC.

Purification by a polymer gel column:

The dry extract or the lyophilizate obtained previously is dissolved in distilled water and the resulting mixture is poured onto a polymer gel column, for example of DIA ION HP20, SEPHADEX LH20, TOYOPEARL HW40 type. Elution is carried out with distilled water, then an alcohol/distilled water mixture in increasing proportions. The fraction containing oenotheine B is identified by HPLC, then lyophilized. The alcohol used is preferably methanol.

Purification by reversed-phase HPLC:

The dry extract or the lyophilizate obtained previously is dissolved in distilled water and then it is purified by reversed-phase HHPLC. Elution is carried out with a gradient composed of a mixture of polar and hydrophilic solvent such as an acetonitrile/water mixture with an acid pH using an acid such as trifluoroacetic acid (TFA). The fraction containing oenotheine B is then isolated as a function of the retention time and of the spectrum obtained by analysis with a diode array detector (210–500 nm) or with a UV detector. After a second optional purification, lyophilization of the expected product is carried out.

In the following examples, there are described several preferred embodiments to illustrate the invention. However, it should be understood that the invention is not intended to be limited to the specific embodiments.

EXAMPLE 1

Extraction from the leaves and branches of *Epilobium parviflorum* with the acetone/water mixture and obtaining of crude oenotheine B.

1275 g of dried and broken up leaves and branches of *Epilobium parviflorum* were introduced into a 100 liter reactor and 20 liters of an acetone-water mixture (7-3) were added. The mixture was stirred with a mechanical stirrer for 60 hours. The mixture was filtered and the leaves were rinsed with 4 liters of acetone. The filtrate was concentrated under reduced pressure at 35° C. to a volume of about 6 liters in such a way that the acetone was evaporated. The remaining aqueous phase was extracted successively twice with 1 liter of diethyl ether, twice with 1 liter of ethyl acetate and twice with 0.5 liter of butanol. After evaporation of these first two fractions under reduced pressure at a temperature of 35° C., 100 g of black resin and 10 g of a friable brown foam were respectively obtained and after evaporation of the third fraction under very reduced pressure at a temperature of 50° C., 45 g of a black resin were obtained which fraction was the richest in oenotheine B.

EXAMPLE 2

Extraction from leaves and branches of *Epilobium parviflorum* with water to obtain crude oenotheine B.

20 g of crushed leaves and branches of *Epilobium parviflorum* were covered by 350 ml of water at 65° C. and the mixture was mechanically stirred for 20 hours at ambient temperature. The mixture was filtered and the leaves were rinsed with 100 ml of distilled water to obtain 450 ml of a clear black solution. A lyophilization of 50 ml of this solution provided 500 mg of a pale green powder rich in expected product.

EXAMPLE 3

Identification and purification of oenotheine B

The lyophilizate of Example 2 was dissolved in 2 mg/ml of distilled water. 10 ml (20 mg) were injected onto a preparative column of NOVAPACK™ type (C18 6 µ7.8× 300 mm). Elution was carried out by a solvent gradient at a flow rate of 5 ml/min under the following conditions (volume percentages):

0–2 min sample

2–7 min 100% water with 0.1% v/v of trifluoroacetic acid (TFA),

7–57 min linear gradient of 0 to 10% v/v of acetonitrile with 0.1% v/v TFA,

57–77 min linear gradient of 10 to 25% v/v of acetonitrile with 0.1% v/v TFA,

77–97 min linear gradient of 25 to 90% v/v of acetonitrile with 0.1% v/v TFA.

Detection was carried out using a diode array at wavelengths ranging from 210 nm to 400 nm. Of the 43 fractions collected, only one had an activity vis-a-vis 5α-reductase and the retention time was between 36 and 38 min. After the purity was checked, this fraction was lyophilized. The expected product was immediately analyzed by NMR and mass spectrometry. The NMR and mass analyses of this fraction were comparable with those described in the literature (HATANO et al., J. Chem. Soc. Perkin Trans, Vol. 1 (1990), pp. 2735–2743).

NMR 250 MHz, Solvent: acetone-$d_6$, at 45° C. Ref SiMe$_4$, (ppm), J (Hz) alpha glucose beta glucose H-1 6.20 d J=3.5 H-1 4.42 d J=8

H-2 5.87 dd J=3.5–10.5 H-2 5.16 dd J=8–9.5
H-3 6.11 dd J=10.5 H-3 5.45 t J=9.5
H-4 5.59 t J=10.5 H-4 4.90 t J=9.5
H-5 4.57 dd J=6–10 H-5 4.13 dd J=5–9.5
H-6 5.24 dd J=6–13 H-6 5.01 dd J=5–13
3.63 d J=13 3.84 d J=13
see Example 4 formula.

Mass Spectrum m/z MALDI (Matrix Assisted Laser Desorption Ionization) 1569 [(M+H)]⁺ 1591 [(M+Na)]⁺ 1607 [(M+K)]⁺

EXAMPLE 4

Purification of oenotheine B

A microbondapack preparative column (C18 10μ, length 50 cm, diameter 2 cm (1 inch)) was used and 1 g of lyophilizate of Example 2 dissolved in 50 ml of water was injected. Elution was carried out with an eluant mixture of water-acetonitrile with 0.1% trifluoro-acetic acid. The gradient of the concentration of acetonitrile was increased by 15% v/v every 30 minutes. The products were detected by means of a UV detector (wavelength 305 nm). The expected product emerged with a retention time of 27 minutes. After lyophilization of the fractions, about 35 mg of the pure expected product were recovered in the form of a beige powder.

UV McOH/HCl 0.1N 218 nM (=120000) and 266 nM (=55000) MeOH 218 nM (log=5.09) and 265 nM (log=4.77) McOH/NaOH 0.1N 285 nM (=33000) and infl. 315 and 473 nM Non-reversible modification.

Circular dichroism

McOH/HCl 0.1N

Max. 219 nM (O)=+3.8 10⁵ infl. 236 nM (O)=+1.7 10⁵

Max. 259 nM (O)=−4.5 10⁴ infl. 282 nM (O)=+9.5 10⁴

NMR at 400 C 13 MHz Solvent: $D_2O$ Temperature: 297 K. for the proton 318 K. for carbon 13.

Reference: TSP at 0 ppm

Abbreviations: (ppm) chemical displacement in ppm J (Hz) coupling constant in Hz.

Multiplicities:

s singlet ws wide singlet d doublet dd doublet of doublets t triplet

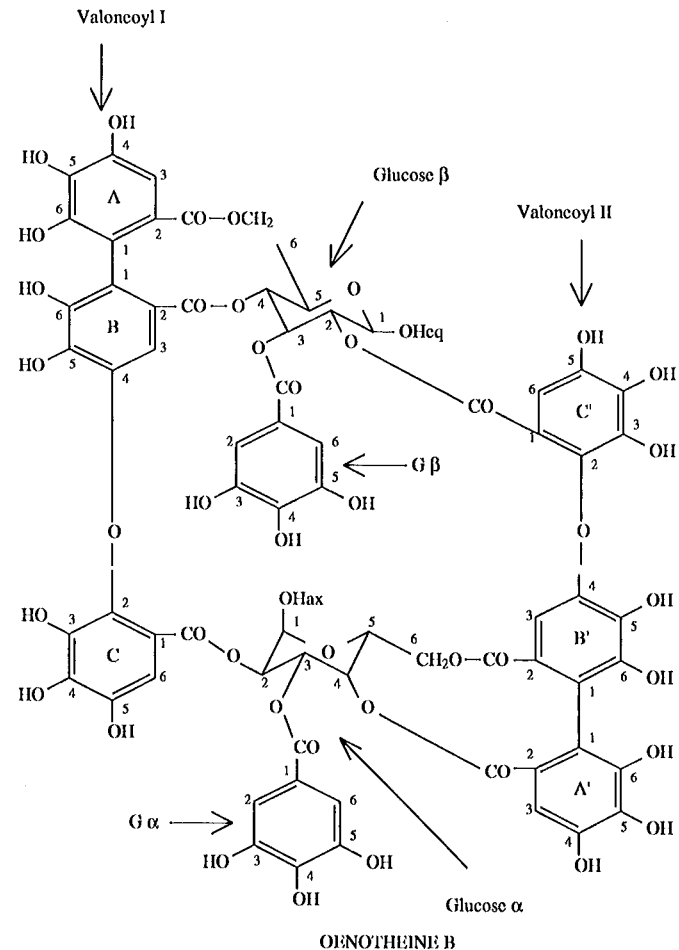

OENOTHEINE B

| Residue | N° | δ (ppm) $^1$H | Multiplicity (proton) | $^3$J (Hz) proton | δ (ppm) $^{13}$C |
|---|---|---|---|---|---|
| Glucose α | 1 | 5,67 | d | 3,5 | 92,8 |
| | 2 | 4,80 | dd | 3,5–10 | 77,4 |
| | 3 | 5,87 | dd | 10 | 73,7 |
| | 4 | 5,61 | t | 10 | 72,7 |
| | 5 | 4,70 | dd | 6,5–10 | 70,7 |
| | 6 | 4,00 | d | 13,5 | 66,5 |
| | | 5,34 | dd | 6,5–13,5 | |
| Glucose β | 1 | 4,74 | d | 8 | 97,9 |
| | 2 | 5,27 | dd | 10–8 | 77,8 |
| | 3 | 5,51 | t | 10 | 75,5 |
| | 4 | 5,15 | t | 10 | 74,1 |
| | 5 | 4,24 | dd | 10–5 | 74,2 |
| | 6 | 4,04 | d | 13,5 | 67,0 |
| | | 4,87 | dd | 5–13,5 | |
| Galloyl α | 1 | — | | | 124,4 |
| (Gα) | 2–6 | 6,90 | s | — | 112,4 |
| | 3–5 | — | | | 147,6 |
| | 4 | — | | | 140.9 |
| | C=0 | — | | | 171,6 |
| Galloyl β | 1 | — | | | 122,7 |
| (Gβ) | 2–6 | 7,21 | s | — | 113,6 |
| | 3–5 | — | | | 147,6 |
| | 4 | — | | | 141,8 |
| | C=0 | — | | | 169,0 |
| Valoneoyl I Cycle A | 1 | — | | | 116,6 |
| | 2 | — | | | 126,0b |
| | 3 | 6,73 | s | | 110,4a |
| | 4 | — | | | 148,0 |
| | 5 | — | | | 138,3 |
| | 6 | — | | | 146,4c |
| | C=0 | — | | | 172,0 |
| Valoneoyl I Cycle B | 1 | — | | | 122,9 |
| | 2 | — | | | 128,2b |
| | 3 | 6,49 | sl | | 116,5 |
| | 4 | — | | | 149,5 |
| | 5 | — | | | 144,2 |
| | 6 | — | | | 146,6c |
| | C=0 | — | | | 171,8 |
| Valoneoyl I Cycle C | 1 | — | | | 120,1 |
| | 2 | — | | | 141,6b |
| | 3 | — | | | 129,3b |
| | 4 | — | | | 141,3 |
| | 5 | — | | | 144,9 |
| | 6 | 6,55 | sl | | 112,1 |
| | C=0 | — | | | 171,5 |
| Valoneoyl II Cycle A' | 1 | — | | | 118,1 |
| | 2 | — | | | 128,1b |
| | 3 | 6,63 | s | | 110,3a |
| | 4 | — | | | 148,0 |
| | 5 | — | | | 139,2 |
| | 6 | — | | | 146,8c |
| | C=0 | — | | | 172,6 |
| Valoneoyl II Cycle B' | 1 | — | | | 119,5 |
| | 2 | — | | | 128,5b |
| | 3 | 6,52 | s | | 108,7 |
| | 4 | — | | | 149,6 |
| | 5 | — | | | 138,6 |
| | 6 | — | | | 147,2c |
| | C=0 | — | | | 172,3 |
| Valoneoyl II Cycle C' | 1 | — | | | 118,4 |
| | 2 | — | | | 137,5 |
| | 3 | — | | | 131,6b |
| | 4 | — | | | 142,6 |
| | 5 | — | | | 145,6 |
| | 6 | 6,81 | s | | 113,0 |
| | C=0 | — | | | 170,1 | a - the attributions can be reversed between themselves
b - the attributions can be reversed between themselves
c - the attributions can be reversed between themselves

MASS. SPECTROMETRY

Experimental part

The instrument used for this study was a triple sector and double focus "VG Autospec E" spectrometer (Fison Instrument). The molecular mass of the sample is determined under LSIMS (Liquid Secondary ionization Mass Spectrometry) ionization in positive and negative mode. The sample was dissolved beforehand in a matrix called "Magic Ballet/ TFA" before being bombarded by a primary ion beam from a Cs$^+$ gun. This beam was accelerated under a voltage of 30

KV and had a capacity of 2 to 3μ amps. The secondary ions (sample) were accelerated under a voltage of 8 KV.

Study of the fragmentation was carried out by linked scans by the B/E=Const method. For this, the "parent" ion was fragmented by collision in a cell situated in the first free area of the field (1 FFR). The collision gas introduced into this cell was air, the pressure of which was that necessary to reduce by half the initial intensity of the "parent" ion.

This study was carried out in two stages:

a) Fragmentation of the quasimolecular ion ($MH^+$)

b) Successive fragmentations of each of the ions obtained previously.

Results:

A) Positive mode LSIMS
$MH^+$=1569 Da

B) Negative mode LSIMS $(M-H)^-$=1567 Da

C) Fragmentation of the $MH^+$ ion=1569 Da

The main ions observed in this spectrum were: $1399^+$-$1237^+$-$767^+$-$453^+$

D) Fragmentation of the $1237^+$ ion

The main ions observed in this spectrum were: $1085^+$-$767^+$-$453^+$

E) Fragmentation of the $767^+$ ion $749^+$-$615^+$-$471^+$-$453^+$-$315^+$-$152^+$ F) Fragmentation of the $453^+$ ion Uncharacteristic spectrum throwing up in particular the 435 Da ion (dehydration).

EXAMPLE 5

Purification of oenotheine B 710 mg of the black resin of Example 1 obtained by concentrating the butanol fraction were dissolved in 5 ml of distilled water and poured into a DIA ION HP20 resin column (20 cm×2 cm). Elution was carried out with 200 ml of distilled water, and then 200 ml of a distilled water-methanol mixture (80–20). The second fraction was lyophilized to obtain 58 mg of oenotheine B in the form of a pulverulent beige solid. Others fractions also contained oenotheine B. The NMR, UV, CD and mass spectrometry analyses were identical to those described in Example 4.

Pharmacological study of oenotheine B

The test for measuring the 5α-reductase activity was carried out in vitro by incubating the enzyme and its substrate (testosterone) and by measuring by HPLC chromatography the amount of 5α-reduced metabolites formed (dihydrotestosterone (DHT) and 5α-androstane-diol). Homogenates of human prostates obtained by radical prostatectomies due to benign hyperplasia of the prostate (BHP) were used.

Method

Preparation of the homogenate:

The prostate was collected straight after leaving the operating theater suite and packed in aluminum paper placed in a container filled with dry ice. At the laboratory, if the homogenate was not prepared immediately, the prostate could be stored at −80° C. The prostate was cut into very thin slices on ice, then ground up in medium A [20 mM of potassium phosphate, pH 6.5; 0.32M of sucrose; 1 mM of dithiothreitol (DTT); 50 uM of hydrated sodium salt of triphosphopyridine nucleotide (NADPH)] in a polytron, then in a Potter glass. After centrifuging at 140,000 g for 60 minutes at 4° C., the product was resuspended in 10 to 20 ml of medium B [20 nM of potassium phosphate, pH 6.5; 20% of glycerol; 1 mM of dithiothreitol]. The product was divided into Nunc tubes and stored at −80° C. The proteins were dosed on a small amount of the homogenate for its future use in the test and it was assured of having at least 10 mg of proteins/ml of homogenate.

Measurement of the 5α-reductase activity:

Incubation was carried out at a pH of 5.5 at the rate of 1 ml of medium/tube in the presence of citrate (normal medium of the prostate).

1) Preparation of substrate (S), that is the mixture of "unlabelled" testosterone and "tritiated" testosterone with an isotopic dilution of 100 in a trisodium citrate buffer, pH 5.0.

a) 40 mM of trisodium citrate buffer: 11.76 g of 3Na-citrate, $2H_2O$ (Merk ref. Art 6448) were weighed out, and dissolved in 1 liter of distilled water (Milli-Q) and the pH was adjusted to 5.0.

b) Mixture of "unlabelled" testosterone and "tritiated" testosterone" with an isotopic dilution of 100: To obtain a 1 mM solution of testosterone, 2.88 mg of "unlabelled" testosterone were weighed out which was dissolved in 10 ml of ethanol. This solution was diluted to 0.99/1000 or 9.9 μl in 10 ml of citrate buffer (=$10^{-6}$M solution). 9 μl of testosterone-$^3$H (NET-370) were added to 10 ml of the preceding solution (=isotopic dilution of 100). Substrate (S) was ready.

2) Preparation of the Enzyme+DTT+NADPH mixture a) Potassium phosphate buffer, 40 mM, pH 6.5:

5.44 g of $KH_2PO_4$ (Riedel de Haen ref. 30407) were dissolved in 1 liter of distilled water (Milli-Q) and the pH was adjusted to 6.5.

b) DTT 1 mM (Sigma)

3.1 mg of DTT were dissolved in 1 ml of phosphate buffer.

c) NADPH 500 μM (Sigma) 8.33 mg of NADPH were dissolved in 1 ml of phosphate buffer.

d) Enzyme+DTT+NADPH mixture (E):

0.5 mg of proteins of the prostate homogenate, 50 μl of DTT and 50 μl of NADPH were mixed together at 4° C. for each test. The mixture was adjusted to 500 μl with the phosphate buffer.

3) Incubation:

The same number of tubes was prepared as the number of tests. 500 μl of (S) and 10 μl of inhibitor at the desired concentration (or ethanol for the controls) were put into each tube. The tubes containing mixture (S) and the phial containing mixture (E) to be preincubated were heated in a water bath for 3 to 5 minutes. To start the reaction, 500 μl of E were rapidly transferred into each tube containing (S)+the inhibitor and incubation was carried out at 37° C. with gentle stirring for 30 minutes. The reaction was stopped at the end of the incubation by putting the tubes in ice.

4) Extraction

As soon as the reaction had stopped, 2 ml of ethyl acetate were placed into each tube and stirring was carried out with a Multi-tube vortexer for 1 minute. The tubes were left to decant for 10 minutes, then 1.6 ml of the upper organic phase of the extract (=80%) were recovered in other tubes. After total evaporation of the ethyl acetate, 800 μl of the mobile phase which will be used in the HPLC were added to each tube.

5) HPLC chromatography:

The amounts of metabolites produced during the incubation were measured by separating the compounds formed by reversed-phase high performance liquid chromatography (HPLC). An ODS-HYPERSIL column (diameter of particles=5 μm) and a mobile phase composed of McOH/THF/$H_2O$ in a ratio of 45/15/40 were used. The extract collected after extraction was injected automatically onto the HPLC system and by the linear radioactivity measurement system (Berthold), only the radioactive metabolites, formed from the testosterone labelled with the substrate, were evaluated. This measurement was very sensitive and eliminated all the possible endogenic products.

Expression of the results and methods of calculation:

The amounts of metabolites formed were calculated relative to a reference curve entered in the MT2 software of the HPLC. At the level of the MT2, they emerged in pmoles/μl injected. Reference curves exist for testosterone, DHT and androstane-diol, the two 5-α-reduced metabolites of testosterone. The rates were expressed in moles of products formed/mg of homogenate proteins, each test being carried out twice, and the percentage of residual 5α-reductase activity relative to the control tests was calculated:

%=Rates of products formed in presence of inhibitor×100

Rates of products formed for the controls

Result

The $IC_{50}$ for inhibition of the 5α-reductase activity of the control for oenotheine B was $2.2 \times 10^{-5}$M.

Various modifications of the compositions and method of the invention may be made without departing from the spirit or scope thereof and it is to be understood that the invention is intended to be limited only as defined in the appended claims.

What is claimed is:

1. A method of inhibiting 5α-reductase in warm-blooded animals comprising administering to warm-blooded animals in need thereof an effective amount of oenotheine B to inhibit 5α-reductase.

2. A process for the preparation of oenotheine B comprising extracting dried samples of *Epilobium parviflorum* with water or a mixture of water and water-miscible solvents, filtering the extract, optionally concentrating the extract by evaporation of the water-miscible solvents under reduced pressure, subjecting the resulting aqueous phase to a lyophilization or extracting the aqueous phase with a polar solvent and evaporating the extract to dryness to obtain a dry residue and purifying the lyophilizate or dry residue by reversed-phase HPLC or a polymer gel column to obtain oenothoine B.

3. The process of claim 2 wherein the first extraction is effected with an acetone-water mixture.

* * * * *